United States Patent
Nyfors

(10) Patent No.: US 11,016,037 B2
(45) Date of Patent: May 25, 2021

(54) FLUID MEASURING SYSTEM

(71) Applicant: Roxar Flow Measurement AS, Stavanger (NO)

(72) Inventor: Ebbe Gustaf Nyfors, Sandnes (NO)

(73) Assignee: Roxar Flow Measurement AS, Stavanger (NO)

( * ) Notice: Subject to any disclaimer, the term of this patent is extended or adjusted under 35 U.S.C. 154(b) by 220 days.

(21) Appl. No.: 15/568,024

(22) PCT Filed: Jun. 14, 2016

(86) PCT No.: PCT/EP2016/063578
§ 371 (c)(1),
(2) Date: Oct. 20, 2017

(87) PCT Pub. No.: WO2016/202774
PCT Pub. Date: Dec. 22, 2016

(65) Prior Publication Data
US 2018/0113082 A1 Apr. 26, 2018

(30) Foreign Application Priority Data
Jun. 15, 2015 (NO) .................................. 20150773

(51) Int. Cl.
*G01N 22/00* (2006.01)
*G01N 33/28* (2006.01)
*G01F 1/66* (2006.01)

(52) U.S. Cl.
CPC .............. *G01N 22/00* (2013.01); *G01F 1/66* (2013.01); *G01N 33/2847* (2013.01)

(58) Field of Classification Search
CPC ....... G01N 22/00; G01N 33/2847; G01F 1/66
(Continued)

(56) References Cited

U.S. PATENT DOCUMENTS 4,580,441 A * 4/1986 Sakurai .................... F01N 3/028
250/250
5,485,743 A * 1/1996 Taherian ................ G01N 22/00
73/61.44
(Continued)

FOREIGN PATENT DOCUMENTS

CN 105008916 A 10/2015
EP 2500699 B1 3/2015
(Continued)

OTHER PUBLICATIONS

Savage, John, "International Search Report," prepared for PCT/EP2016/063578, dated Oct. 5, 2016, four pages.
(Continued)

*Primary Examiner* — Jeff W Natalini
(74) *Attorney, Agent, or Firm* — Shackelford, Bowen, McKinley & Norton, LLP

(57) ABSTRACT

This invention relates to a system for measuring electrical characteristics of a multiphase fluid flow in a pipe, the system comprising an essentially coaxial insert in said flow defining an annular space between a chosen part of said insert and the pipe wall. The system including resonance measuring means including at least one first antenna, the resonance measuring means being adapted to transmit an electromagnetic signal into said volume within a frequency range comprising at least one predetermined resonance in said volume, the resonance measuring means also being adapted to measure the resonance properties in said volume, said resonance having an amplitude minimum in at least one known position in said volume and said first antenna positioned outside said known position of amplitude minimum. The system also comprising transmission measuring means including a second antenna positioned at, or close to, said known position of amplitude minimum, and being adapted to measure a transmission property between said second (Continued)

antenna and at least one of said first antennas in said resonance measuring means. Based on these measurements the system is adapted to calculate said electrical characteristics.

8 Claims, 2 Drawing Sheets

(58) Field of Classification Search
USPC .......................................................... 324/640
See application file for complete search history.

(56) References Cited

U.S. PATENT DOCUMENTS

| | | | |
|---|---|---|---|
| 2008/0148867 A1* | 6/2008 | Nyfors | G01F 1/40 73/861.63 |
| 2012/0006430 A1* | 1/2012 | Gentile | G01F 1/40 137/561 R |
| 2015/0097579 A1* | 4/2015 | Sharma | G01N 22/00 324/637 |
| 2016/0054161 A1* | 2/2016 | Abou Khousa | G01F 1/708 73/861.04 |

FOREIGN PATENT DOCUMENTS

| | | |
|---|---|---|
| NO | 313647-61 | 11/2002 |
| WO | WO-99063331 A2 | 12/1999 |
| WO | WO-01088513 A1 | 11/2001 |
| WO | WO-03034051 A1 | 4/2003 |
| WO | WO-2011133046 A1 | 10/2011 |
| WO | WO-2013164303 A1 | 11/2013 |
| WO | WO-2014122093 A1 | 8/2014 |

OTHER PUBLICATIONS

Corneliussen, Sidsel, et al., "Handbook of Multiphase Flow Metering," Mar. 2005, pp. 1-116.

Nyfors, Ebbe Gustaf, "Cylindrical Microwave Resonator Sensors for Measuring Materials Under Flow," Thesis for the degree of Doctor of Science in Technology, Report S243, May 2000, Helsinki University of Technology.

* cited by examiner

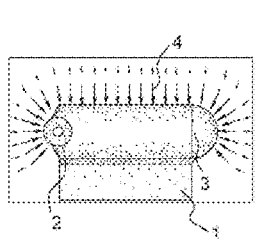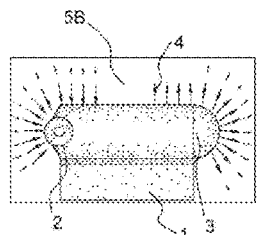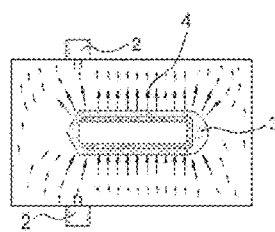
FIG. 1A    FIG. 1B    FIG. 1C
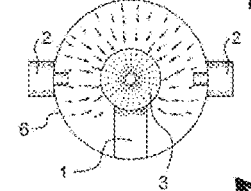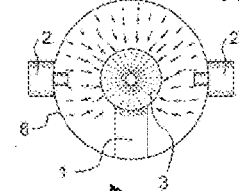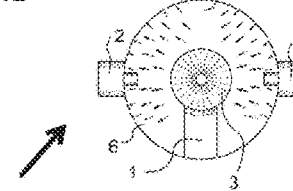
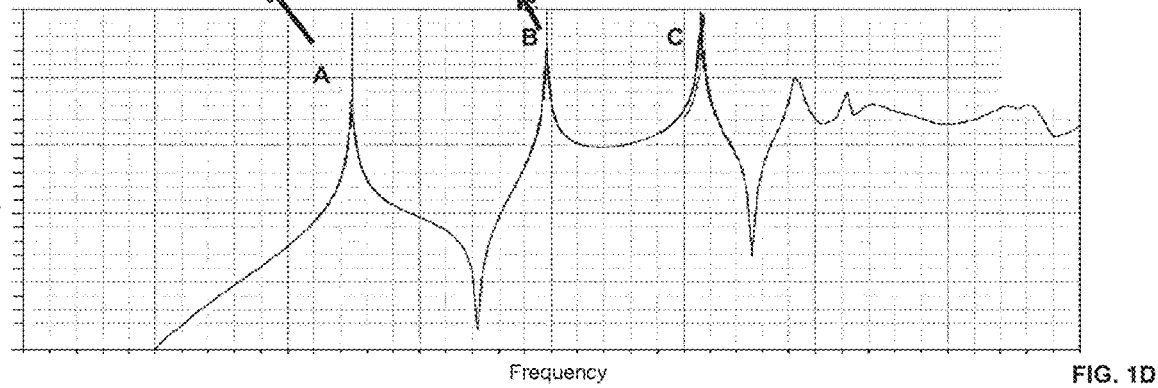
FIG. 1D

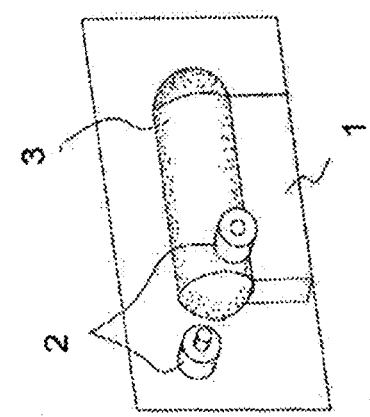
FIG. 2A
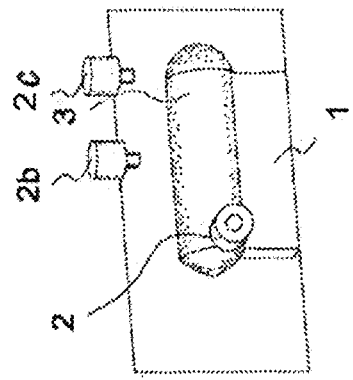
FIG. 2B
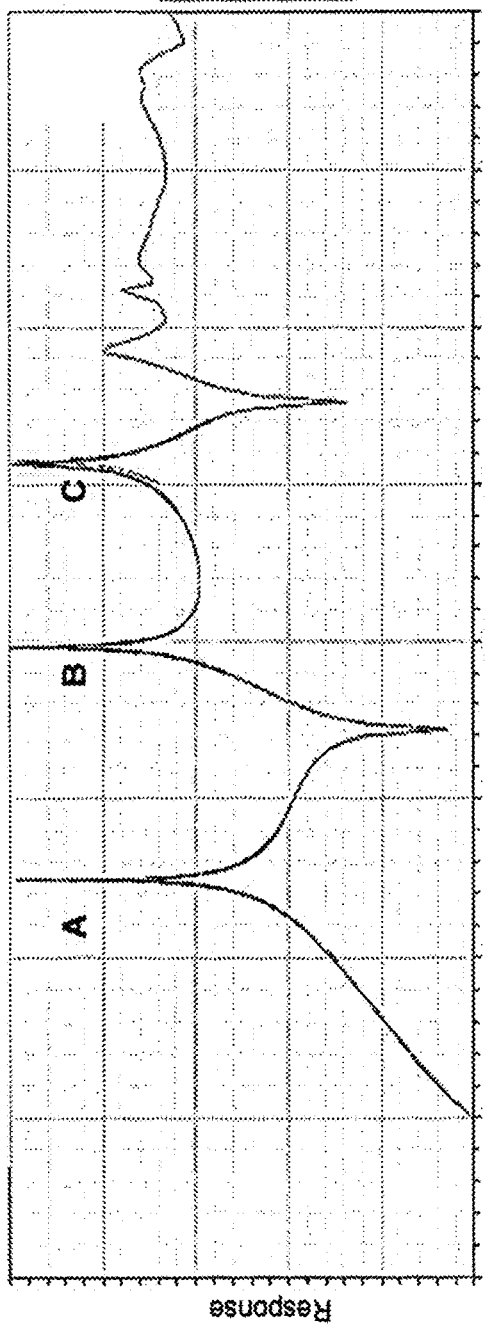
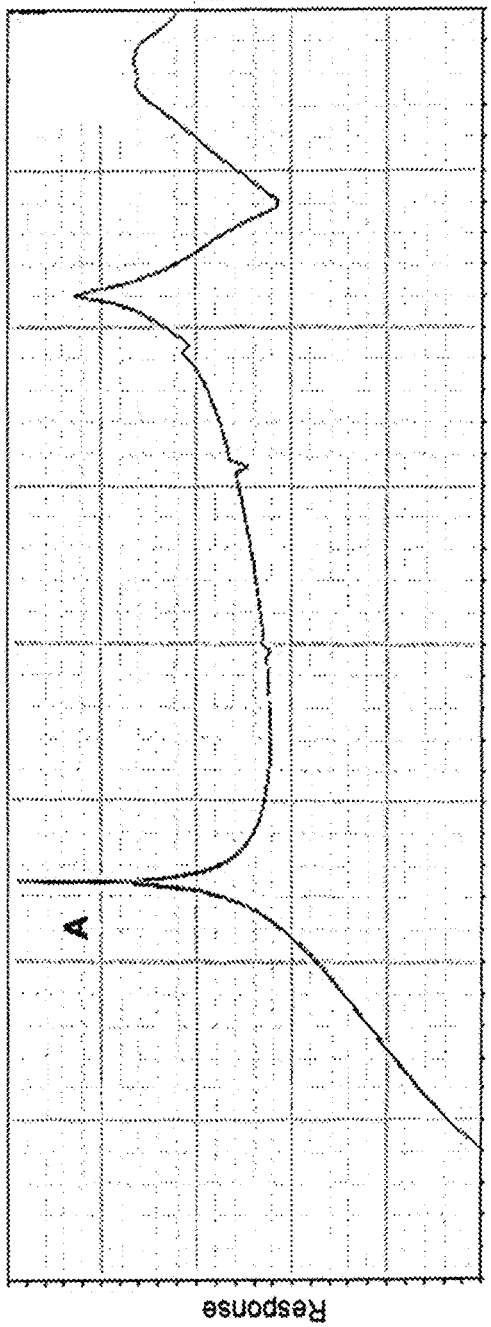

FLUID MEASURING SYSTEM

This invention relates to a measuring system for measuring the characteristics of a fluid flow, especially a multiphase fluid flow comprising a fraction of water.

In oil and gas production and processing it is necessary to monitor the content and properties of the fluid flow, such as the fractions of oil, gas and water, and the salinity of the water, as they will change during the production and will affect the further processing. Several types of technologies have been used to sample the information necessary to find the fractions and the salinity, such as acoustic measurements, pressure, gamma and electrical measurements.

The present invention relates to electrical measurements used to determine the content, e.g. composition and salinity, in mixtures of oil, gas, and water using resonance and transmission characteristics for chosen electromagnetic signals in the flow. This may for example relate to the conductivity of the flow, thus being able to indicate e.g. the salinity and/or the water content in the flow. The latter example is based on the fact that dissolved salts in the water result in the water conductivity. This may be measured in different ways, for example with a system using electromagnetic signals, where the salinity will affect the conditions for electromagnetic signals in or close to the microwave range, and more specifically in the effect of resonance or transmission properties of the electromagnetic signals in the flow, as is discussed in the publications discussed below.

The conductivity depends on the amount and type of ions in the solution, and on the temperature. The water in a multiphase flow in the oil industry may contain several types of ions, but the ones by far most common are Na+ and Cl– from sodium chloride. By salinity we here mean the equivalent amount of sodium chloride, which gives the same conductivity as the actual solution, and it is typically expressed in % weight of the saline water.

As discussed in WO2013/164303 the salinity of the flow may be measured by measuring the transmission properties through the fluid, or by the resonance conditions in a cavity containing the fluid, depending on the characteristics of the fluid, especially related to the loss in the electromagnetic energy transmitted through the fluid. The resonance properties, for example, may be used in fluids having low loss in the relevant electromagnetic frequencies, while measurement of transmission properties may be used when the loss is higher. A resonator for measuring the fluid flowing in a pipe can be formed e.g., by introducing an insert in the pipe. The use of resonance properties relating to different types of inserts is also discussed in WO2013/164303 as well as in WO2014122093, WO 2003/034051 as well as WO99/63331, where a resonating electromagnetic wave in or close to the microwave region is obtained between a conductive pipe and an insert.

In WO2014122093 it is also acknowledged that one may obtain several resonance frequencies, which along with the Q-factor of the resonance peak may be used to characterize the flow conductivity. More specifically, a solution is discussed aimed at improving the conductivity measurements by providing and measuring the electromagnetic field at two resonances in terms of the resonant frequencies and Q-factors. The different resonant frequencies in WO2014/122093 may be obtained in several different ways. One of them may be the coaxial TEM mode discussed in EP2500699B1, while others may be higher-order resonances of the TEM-mode, or so-called waveguide modes (see below) obtained by constructing the insert or placing probes comprising antennas or transducers in a specific way.

A problem related to the solution described in WO2013/164303 is that there may be situations, when the medium is neither clearly a high-loss nor a low-loss medium. The quality of the resonance is then too poor to be used for measurements and the transmission measurements should probably be used instead, but the resonance is still strong enough to affect the transmission measurements, and thus typically interfering with the transmission signal and resulting in a reduced quality of the measurements.

In NO313647 a measuring system for measuring permittivity of a fluid is discussed using a transmitter and a receiver antenna for resonance measurements, where the positions of the antennas are chosen to limit the effect of other resonance modes.

Thus the measurements of the dielectric properties of a fluid for determining e.g. the composition or the salinity of the water component can be performed using an electromagnetic (e.g. microwave) resonator sensor, when the fluid is a low-loss fluid, and using transmission measurement, when the fluid is a high-loss fluid. The resonator properties, which are determined from a measured frequency response, are typically the resonant frequency and/or the Q-factor. The resonator properties can usually be measured using a single antenna by measuring the reflection coefficient as a function of frequency, or using two antennas, in which case one antenna excites the resonance and the other one senses the resulting electromagnetic fields. When the frequency is swept past the resonance frequency, a resonance peak is displayed in the frequency response. Transmission measurement here means that an electromagnetic wave is transmitted with a first antenna and received after propagation by one or several other antennas. The transmission properties, which are determined, are typically the phase change and/or the attenuation resulting from the propagation of the signal through the fluid from one antenna to the other.

It is an object of the present invention to reduce the interference of the resonance(s) on the transmission signal, therefore obtaining improved quality of the measurements when combining resonance and transmission measurements in the same section of the pipe, e.g. as described in WO2013/164303. This is obtained as specified in the accompanying claims.

There are in principle no differences between transmitting and receiving antennas, or antennas for performing resonance or transmission measurements, although they may differ due to practical reasons. The same antennas may, therefore, be used both for transmitting waves or exciting resonances, and for receiving signals or sensing electromagnetic fields. Individual antennas mentioned in the description of the invention may be used for more than one purpose. In the present discussion, they will be called according to the use being discussed, not excluding the possibility that they may be called differently in other parts of the description, when other uses are discussed.

As an example, a resonance antenna in the resonance measuring means may transmit electromagnetic signals into the resonator and also receive and measure the resonance properties, such as resonance frequency and Q-factor, based on principles described in the known art. When using a single resonance antenna, the same antenna may both transmit and receive, but in other systems, one resonance antenna may be a transmitter and another antenna a receiver.

Similar as for the transmission measuring means, the antenna positioned in the minimum will in the shown examples be a transmitting antenna, but the system may be reconfigured so as to receive a specific signal from at least one of said first antennas in the resonance measuring means.

From the transmission measuring means, the phase of the signal transmitted between the transmitting and receiving antennas in the resonance and transmission measuring means may be found. In addition to phase, damping and other properties may be found. In addition, when using more than two antennas the differential phase signal obtained through different propagation paths through the flow may be used. The advantages of differential measurements in measurement systems need not be mentioned in this disclosure because said advantages are known to the person skilled in the art of electrical circuits and measurements. Said advantages commonly include, rejection of large common-mode signals that helps reduce requirements on the measurement system, rejection of common-mode noise, and reduced drift.

In the present invention the disclosed positioning of the antennas provides an easier separation between the transmission and resonance signals by utilizing the fact that higher resonance frequencies as discussed in WO2014/122093 will have interference minima where the amplitude at a certain frequency will be zero or at least low enough not to interfere with the transmission signal.

The invention will now be described more in detail below, referring to the accompanying drawings illustrating the invention by way of examples.

FIGS. 1A-D illustrate the different resonances around a cylindrical insert mounted to the pipe wall with a conductive support fin.

FIGS. 2A and 2B illustrate the measured signal at two different positions.

FIGS. 1A, 1B and 1C illustrate the resonating electromagnetic field 4 around a conductive fin 1 and cylindrical insert 3 positioned in a pipe 6 of conductive material thus providing a microwave cavity resonator. The cylindrical insert 3 creates an annular space in the pipe 6 for fluids to pass through. FIG. 1D illustrates a plot of measurements showing a response curve of the system. A frequency sweep is applied at antennas 2 positioned at the end of the fin 1 and insert 3, and electrical response at the antennas 2 measured.

As is illustrated in FIGS. 1A-D the field 4 at three different resonances A, B, C will be distributed differently along and around the insert depending on the frequency. The response as shown in FIG. 1D is an amplitude response. In the first resonance mode A the field 4 has an even distribution along the insert 3 as well as around it except close to the supporting fin 1, where pipe, insert 3 and fin 1 is made from a conductive material. Following the convention introduced in Ebbe Gustaf Nyfors, "*Cylindrical microwave resonator sensors for measuring materials under flow*", Thesis for the degree of Doctor of Science in Technology, Report S243, May 2000, Helsinki University of Technology (ISBN 951-22-4983-9), this mode is called $TE_{1/210}$. Thus, the resonance and Q-factor may be measured at any radial and axial position along the insert 3.

The next resonance mode, called $TE_{1/211}$, when increasing the frequency, however, has a minimum 5B in the longitudinal direction at the middle of the insert. Thus, an antenna in this axial position will measure no, or low, amplitude at the resonant frequency.

At the third resonance mode, called $TE_{110}$, the minimum 5C is at the plane along the pipe direction, on the opposite side from the fin support. Thus, an antenna in this radial position will measure no, or low, amplitude at the resonant frequency.

Thus a resonance measuring antenna being able to measure all these three resonances will have to be positioned outside these two minima 5B, 5C, e.g. as illustrated in an axial plane perpendicular to the plane defined by the support fin, close to the end of the insert.

Higher resonance orders may also be used, both for measuring resonance frequencies and for determining the position of the second antenna 2b.

The simulation results exemplified in the plots are for a pipe with an inner diameter of 125 mm, and an insert with an approximate relative size as shown in the figures. The frequencies A, B and C as shown in the plot are about 620 MHz, 999 MHz, and 1280 MHz respectively. A person skilled in the art will understand that the frequencies depend on dimensions of the various components, including the pipe inner diameter, and the shape and size of the insert. In addition, some modes (like the second mode shown in this example) also depend strongly on the length of the insert.

By response, it is meant signal parameter such as insertion loss, which is attenuation of the signal between the transmitting and receiving antennas. However, the category signal parameter also includes attenuation, amplitude, power, relative power, voltage or current, for example of the signal in the antenna. A similar response diagram as shown in FIG. 1D could also be made for the phase of the signal. The choice of a response parameter depends on the measurement system architecture, and may be influenced by factors such as ease of measurements, etc. Response may even comprise a combination of several signal parameters. The invention is not limited by a specific measurement system, so selection of a measurement system or circuit is not relevant to this disclosure. The response typically comprises transmission related parameters especially when measured on the receiving antenna, but it is also possible to derive least some of the transmission related parameters by measurements on the transmitting antenna.

FIG. 2A illustrates the measurements obtained by an antenna 2 at one end of the insert, in the plane perpendicular to the fin support, clearly showing three resonance peaks corresponding to the three peaks discussed in relation to FIG. 1.

FIG. 2B showing yet another embodiment, on the other hand, illustrates the measurements made by antenna 2b in the position on the opposite side of the pipe seen from the fin support, in the middle of the insert. As can be seen from the figures, the second and third resonances are not seen in that position.

Thus, in order to avoid influences from the resonance frequencies an antenna for performing transmission measurements may advantageously be positioned in a minimum of the higher resonance modes of the resonating fields.

A resonance has a resonant frequency, where the resonance phenomenon is strongest. The resonance, which is seen as a peak in a frequency response like in FIG. 2, also affects the frequency response at frequencies on both sides of the resonant frequency, because the peak has a finite width. The higher the losses, the broader a peak becomes. If a frequency response displays several resonance peaks, they may start to overlap in the region between the peaks, when the losses increase, if the distance in frequency is not large enough. In such a case, there are no frequencies even between the resonances, where transmission measurements could be performed without that the resonances disturb the measurements. Therefore it is advantageous to eliminate coupling to as many resonances as possible to create a frequency region free from interference from resonances, when transmission measurements are performed.

By positioning of the transmitter antenna 2b in the position of the minima, the transmission signal may be used without interference at these frequencies to either designated receivers, or to resonance antennas 2 being able to receive the signals as discussed in WO2013/164303. The system as proposed is thus able to reduce the interference between the two measuring methods and the quality of the measurements under varying conditions.

For providing the combined resonance and transmission measurements it is possible to use two antennas 2 and 2b as shown in FIG. 2B, where the first antenna 2 transmits and measures the resonance frequencies while the second antenna 2b transmits the signals into the cavity for measuring transmission properties in a high loss situation.

Alternatively, two resonance measuring antennas can be used, in such case a second resonance measuring antenna 2c being shown in FIG. 2B. If the distance from the transmitter antenna 2b to the first resonance measuring antenna 2 and the second resonance measuring antenna 2c differ by a known length, the difference in distance may also be used for measuring the transmission properties through the fluid.

Electromagnetic field comprises electric as well as magnetic components. The previous embodiments, for the sake of simplicity, related more generally to the electric field measurements. Magnetic field was generally ignored. Electric and magnetic field are usually distributed differently, so in previous embodiments, antennas coupling more specifically to electric field were discussed, for example, by defining the antenna placement relative to a location where the electric field has an essentially zero power.

In an alternate embodiment, antennas coupling to the magnetic field can be used, for example, loop antennas for the magnetic field. In this embodiment, with antennas coupling to the magnetic field, corresponding measurement can be used to locate the transmitting antenna for transmission measurements in a zero of the magnetic field. Equivalent measurement philosophy as disclosed in previous embodiments can be used for the proposed magnetic embodiment.

In yet another embodiment, the invention comprises both electric and magnetic antennas.

The system according to the present invention thus relates generally to the measuring of electrical characteristics of a multiphase fluid flow in a pipe, such as salinity. The system comprising an essentially coaxial insert 3 in said flow defining an essentially cylindrical or more specifically, an annular volume between a chosen part of said insert and the pipe wall 6 constituting a microwave resonance cavity, the pipe and insert being made from an electrically conductive material.

The system includes resonance measuring means including at least one first antenna, which may be called a resonance antenna. The resonance measuring means is adapted to transmit an electromagnetic signal through the resonance antenna into said volume within a frequency range comprising at least one predetermined resonance in said volume. The system or resonance measuring means is also adapted to measure the resonance properties in said volume through the same resonance antenna or another antenna coupled to the resonance measuring means. The chosen resonance has an amplitude minimum in at least one known position in said volume and said first antenna or antennas is positioned outside said known position of amplitude minimum.

Preferably the frequency range includes at least two resonance frequencies, at least one of which having a minimum amplitude at said known position.

The system also comprising transmission measuring means including a second antenna 2b positioned at, or close to, said known position of amplitude minimum 5B,5C. The second antenna 2b may for simplification be called transmission antenna, although it is possible to use measurements of signals transmitted from the resonance antennas to the transmission antenna related to the transmission measuring means. The transmission measuring means is adapted to provide a transmission property based on the signal propagating between said second antenna and at least one of said first antennas in said resonance measuring means.

The resonance and transmission properties may then be used to provide a measure of the electrical characteristics based on said resonance and transmission properties, as is described in the known art.

The resonance and transmission measuring means may be constituted by separate units coupled to the measuring system or be implemented in the hardware only differing in the programming and use of the antennas.

The system also comprising at least one transmission antenna 2b positioned in said known position 5B, 5C having a low amplitude at one resonance frequency. Preferably the transmission antenna is adapted to transmit a signal being received by at least one resonance antenna, but may also be able to receive a signal transmitted from the resonance antenna.

The system is also adapted to measure said at least two resonance properties and measure the transmission properties, i.e. the phase and/or attenuation, between said resonance and transmission antennas.

Preferably, the system may include two resonance antennas 2 and 2c and one transmission antenna 2b, the transmission antenna 2b being adapted to transmit a signal with a known content. The resonance antennas 2 and 2c may then be placed at different distances from the transmission antenna 2b, and thus be able to measure the difference in transmission properties from the transmission antenna 2b to each resonance antenna 2 and 2c. This way the propagation properties of the signal through the flow may be measured.

The chosen frequency range used in a frequency sweep may be chosen so as to include three resonance frequencies within said volume, the transmitter antenna being positioned in an amplitude minimum for a chosen number of resonance modes.

As is illustrated the insert 3 may have a cylindrical shape with a chosen length, providing a cylindrical volume in the pipe direction. At least one resonance antenna 2 is positioned close to one end of said insert and the transmitter antenna 2b being positioned at equal distances from the insert ends, thus being in the minimum 5B of the first longitudinal resonance.

The cylindrical insert 3 is coupled to the pipe wall 6 through one elongated, conductive fin 1 stretching an essential part of the insert length, so as to limit the propagation of electromagnetic signals along the circumference of the cylindrical cavity, locking the position of the resonance minima 5C in the tangential direction in the cylindrical volume.

The invention claimed is:

1. A system for measuring electrical characteristics of a multiphase fluid flow in a pipe, the system comprising:
a coaxial cylindrical insert in the flow defining an annular cylindrical volume between a part of the coaxial insert and the pipe wall, the coaxial insert being coupled to the pipe wall through a single conductive fin positioned in the cylindrical volume, the annular volume including the flow, the coaxial insert comprising a resonator for electromagnetic signals within a predetermined frequency range, the predetermined frequency range comprising at least one resonance frequency mode having a minimum amplitude at a known position locked by the position of the fin, at said at least one resonance frequency mode;

resonance measuring means comprising at least one resonance antenna, the resonance measuring means being adapted to transmit an electromagnetic signal within the frequency range into the annular volume;

wherein the resonance measuring means is adapted to measure the resonance properties in the volume and the resonance antenna is positioned outside the known position of minimum amplitude;

transmission measuring means comprising a transmission antenna positioned at the known position of amplitude minimum and adapted to measure a transmission property between the transmission antenna and at least one of the resonance antennas; and wherein the system is adapted to calculate electrical characteristics based on the resonance when the fluid is a low-loss fluid, and transmission properties when the fluid is a high-loss fluid.

2. The system according to claim 1, wherein the frequency range comprises at least two resonance frequency modes, at least one of which having a minimum amplitude at the known position.

3. The system according to claim 1, wherein the resonance property comprises at least one of the following: Q-factor and frequency.

4. The system according to claim 1, wherein the transmission property comprises at least one of the following: attenuation, phase difference, and phase.

5. The system according to claim 1, comprising two resonance antennas, the transmission antenna being adapted to transmit a signal with a known content and the resonance antennas having different distances from the transmission antenna, the system being adapted to measure the difference in transmission properties from the transmission antenna to each of the two resonance antennas, thus to measure the propagation properties of the signal through the flow.

6. The system according to claim 1, wherein the frequency range comprises three resonance frequency modes within the volume.

7. The system according to claim 1, wherein:
the insert has a cylindrical shape with a chosen length, providing a cylindrical volume in the pipe direction;
the at least one resonance antenna is positioned at one end of the insert; and
the transmission antenna is positioned equidistant from the insert ends in the axial direction of the insert, thus being in a minimum of a first longitudinal resonance.

8. The system according to claim 7, wherein the cylindrical insert is coupled to the pipe wall through one elongated, conductive fin stretching a part of the insert length.

\* \* \* \* \*